United States Patent [19]

Hursting et al.

[11] Patent Number: 5,830,681
[45] Date of Patent: Nov. 3, 1998

[54] IMMUNOASSAYS FOR AND MONOCLONAL ANTIBODIES TO PROTHROMBIN ACTIVATION PEPTIDE F1.2

[75] Inventors: Marcie J. Hursting, Durham; Bryan T. Butman, Walkersville; Jerald P. Steiner; Bryant M. Moore, both of Bahama, all of N.C.; Frederick A. Dombrose, Ventura, Calif.

[73] Assignee: Akzo Nobel N.V., Arnhem, Netherlands

[21] Appl. No.: 175,482

[22] Filed: Dec. 30, 1993

Related U.S. Application Data

[63] Continuation of Ser. No. 431,964, Nov. 6, 1989, abandoned.

[51] Int. Cl.$^6$ .................................................. G01N 33/53
[52] U.S. Cl. ..................... 435/7.94; 435/7.9; 435/7.92; 435/7.93; 435/7.95; 435/70.21; 435/326; 435/327; 435/337; 530/387.1; 530/387.2; 530/388.1; 530/388.25; 436/501; 436/518; 436/547; 436/548
[58] Field of Search ............................... 435/7.9, 7.1, 7.4, 435/7.91, 7.92, 7.94, 69.6, 70.21, 172.2, 240.26, 965, 975, 240.27; 436/501, 518, 547, 548; 530/387.1, 391.1, 387.9, 388.1, 388.25; 935/89, 106

[56] References Cited

U.S. PATENT DOCUMENTS 5,071,954  12/1991  Pelzer et al. ........................... 530/324

FOREIGN PATENT DOCUMENTS 0303983  2/1989  European Pat. Off. .

OTHER PUBLICATIONS

Pelzer, H. and Stuber, W., "Detection of Prothrombin Activation Fragments $F_2/F_{1+2}$ by an Antibody Against a Synthetic Peptide," Haemostasis 1988, 18 Suppl. 2:Abstract #102.

Shi, Q. et al., "Detection of Prothrombin Activation with a Two-Site Enzyme Immunoassay for the Fragment F1.2," Thromb. Haemostas. 1989, 63:165, Abstract #493.

Davie, E.W. et al., "Cloning of Vitamin K–Dependent Clotting Factors," Dev. Biochem., 1983, vol. 25, Calcium–Binding, pp. 45–52.

Köhler et al, Nature, vol. 256, Aug. 7, 1975, pp. 495–497.

Lee et al, Chemical Abstracts, vol. 98, 177292w, 1983, p. 487.

Oellerich, J. Clin. Chem. Clin. Biochem, vol. 22, 1984 pp. 895–904.

Degen et al, Biochemistry, vol. 22, 1983, pp. 2087–2097.

Lau et al, The Journal of Biological Chemistry, vol. 254, No. 18, 1979, 8751–8761.

Rabiet et al, The Journal of Biological Chemistry, vol. 261, No. 28, 1986, 13210–13215.

Walz et al, Proc. Natl. Acad. Sci. USA, vol. 74, No. 5, May 1977, pp. 1969–1972.

*Primary Examiner*—Laurie Scheiner
*Attorney, Agent, or Firm*—Gregory R. Muir; Mary E. Gromley; William M. Blackstone

[57] ABSTRACT

Monoclonal antibodies and fragments thereof, with binding specificity for an epitope on the carboxy terminus of prothrombin activation peptide F1.2, which can be used in immunoassays to predict thrombosis by measuring the extent of activation of prothrombin. These monoclonal antibodies are also included in a kit for performing such immunoassays.

8 Claims, 9 Drawing Sheets

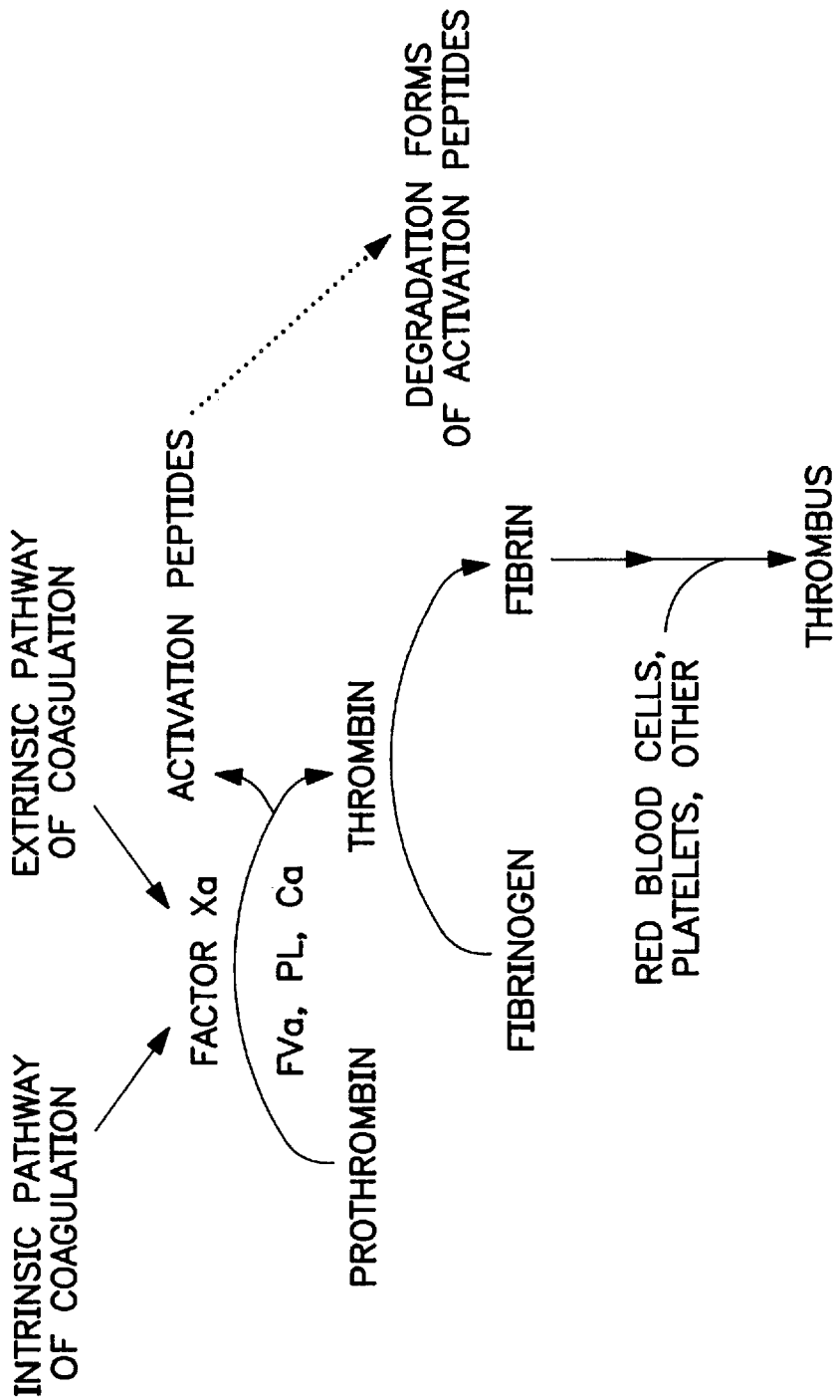
FIG. IA

IMMUNOASSAYS FOR AND MONOCLONAL ANTIBODIES TO PROTHROMBIN ACTIVATION PEPTIDE F1.2

This is a continuation of application Ser. No. 07/431,964 filed Nov. 6, 1989 now abandoned.

BACKGROUND OF THE INVENTION

This invention relates to the field of coagulation, and in particular, monoclonal antibodies raised to epitopes of prothrombin activation peptides F1.2 and F1.2.3 and their degradation products des-R F1.2, F2 and des-R F2 ("Antigens"), their use and the use of fragments of such monoclonal antibodies, in immunoassays to detect Antigens and as components of diagnostic kits.

Thrombosis is a serious and often fatal disease in which blood clots (thrombi) interfere with the normal flow of blood in blood vessels or the heart. Fibrin is a protein generated from the action of the blood coagulation protein thrombin on fibrinogen. A thrombus is a deposit of blood components, primarily fibrin with red blood cells or aggregated platelets on the lining or surface of a blood vessel or cavity of the heart. A thrombus includes insoluble fibrin polymers that are later decomposed through fibrinolysis. Thrombi can obstruct normal blood flow, leading to serious and often fatal consequences.

Over 64 million Americans are affected by cardiovascular disease (CVD), a disorder associated with increased risk of thrombosis. CVD, which includes heart attack, stroke, high blood pressure, artherosclerosis, rheumatic heart and congenital heart defects, accounts for greater than fifty percent of all deaths in the United States. Over 4.8 million Americans have a history of heart attack, angina pectoris or both. In 1989, it is estimated that 1.5 million new heart attacks will occur, with 45% happening to people under the age of 65; over 75% will require hospitalization and over one-third will die. Almost two million stroke victims are alive today with approximately 500,000 people suffering strokes each year. One-fifth of total CVD fatalities are under the age of 65. Annual health care costs for CVD were expected to exceed $83 billion in 1988.

Other disorders also exhibit an increased tendency to thrombosis. These include, but are not limited to cancer, pregnancy, aging, trauma, oral contraceptive use, diabetes mellitus, liver and kidney disease, and obesity.

Minimizing the risk of thrombosis to patients on anticoagulant therapy is another area of patient treatment in the field. When an anticoagulant is administered, it is necessary to determine the desired levels of the drug to maintain effective therapy. Currently the appropriate dosage for oral anticoagulant therapy is established by monitoring the patient's prothrombin time ("PT"), which is maintained at approximately one and one-half to two and one-half times that obtained with normal plasma. The approximate dosage for heparin therapy is often established by monitoring the patient's activated partial thromboplastin time ("APTT"), which is maintained higher than 1.5 times the control.

Blood coagulation is a highly complex process, not totally understood even today. The final stage of the coagulation pathway results in the formation of fibrin, a component required for thrombus formation. Prothrombin activation and the associated generation of thrombin are required for fibrin formation. Activation of prothrombin in the coagulation cascade is shown in FIG. 1A, and prothrombin activation products and degradation forms are shown in FIG. 1B. Factor Xa catalyzes prothrombin activation in the presence of coagulation factor Va, calcium and stimulated platelets, cleaving prothrombin at two sites, Arg 271-Thr 272 and Arg 320-Ile 321, to produce the prothrombin activation peptide fragment F1.2 and thrombin. The former cleavage exposes a carboxy terminal on F1.2 not present on prothrombin that contains epitopes unique to F1.2. Thrombin can degrade F1.2 by a single cleavage (Arg 155-Ser 156), yielding prothrombin fragment F1 and prothrombin fragment F2. Rabiet, M. J., 261 J. Biol. Chem. 13210–13215 (1986) has suggested that prothrombin activation peptide fragment 1.2.3, a peptide thirteen amino acids longer than F1.2, is formed in clotting plasma by cleavage at Arg 284 Thr 285. F1.2.3 is very labile and can be detected only when protease inhibitors are present.

In circulation, plasma carboxypeptidase may further degrade F1.2 or F2 by removing from the carboxy terminus the last amino acid, arginine ("R"), to generate degradation products des-R F1.2 or des-R F2. This is postulated based on the work of Chenowith and Teger-Nilsson, (Chenoweth, D. E., 75 Proc. Natl. Acad. Sci. USA 3943–3947 (1968); Teger-Nilsson, A. C., 22 Acta Chem. Scand. 3171 (1968)), who have demonstrated a des-R form of complement component C5a and fibrinopeptide B, which are known substrates for circulating carboxypeptidase. Carboxypeptidase preferably cleaves the terminal arginine if a glycine or alanine immediately proceeds the terminal arginine. (McKay, T. J., 197 Archives Biochem. Biophysics 487–492 (1979)). Glycine is positioned immediately prior to the terminal arginine of the carboxy terminal sequences of F1.2 and F2 and both are expected to be good substrates for carboxypeptidase and therefore cleaved.

F1.2 consists of 271 amino acids and circulates with a half-life of about ninety minutes. (Bauer, K. A., 76 J. Clin. Invest. 826–836 (1985)). It can be defined as containing two regions, F1 and F2. The F1 region contains a special calcium-binding amino acid, gamma carboxyglutamic acid, which is necessary for F1, F1.2 and prothrombin to assume normal, calcium dependent conformations required for normal phospholipid binding activity.

Generation of Antigens indicates thrombin formation and the activity of coagulation factor Xa. Currently it is known that F1.2 levels are elevated in clinical states associated with increased risk of thrombosis, and are decreased during anticoagulant therapy. (Bauer, K. A., 70 Blood 343–350 (1987)). Measurement of such levels are important to patient care.

The formation of thrombin and Antigens need not be coincident with fibrin formation, since thrombin has many natural substrates and inhibitors. But as more prothrombin activation occurs, the amount of thrombin also increases and the possibility that fibrin formation and perhaps thrombus formation will occur increases. Conversely, as less prothrombin activation occurs, the amount of thrombin available to cleave fibrinogen and the possibility of thrombus formation also decreases.

Currently, many tests exist for predicting and diagnosing bleeding problems in coagulation, as well as for diagnosing active thrombosis. For example, PT is a one-stage coagulation assay that tests the overall integrity of a portion of the coagulation system which includes factors VII, X and V, prothrombin and fibrinogen, and is useful when oral anticoagulants are being administered to a patient. As described earlier, APTT is useful in monitoring heparin anticoagulant therapy. Radioimmunoassays are also available to measure native and abnormal prothrombin levels.

There are a few immunological tests that measure the result of thrombin activity, including fibrinopeptide A, and soluble fibrin. Levels of fibrinopeptide A are elevated with overt thrombosis but there is poor correlation between concentration of fibrinopeptide A and risk of thrombosis. A polyclonal antibody-based immunoassay for thrombin-antithrombin III complex is available which measures circulating concentration of inactive thrombin that is bound by its main physiological inhibitor, antithrombin III.

Later in the coagulation process, fibrinolysis of the formed thrombus by plasmin occurs and can be measured by several immunological tests, such as D-Dimer, total degradation products and fibrin degradation products.

None of the above-described assays are proven to be predictive of thrombosis.

No highly sensitive monoclonal antibody based test is currently available for measuring the extent of activation of prothrombin. Such a test would be useful to identify patients at increased risk of thrombosis, improve management of patients on anticoagulant therapy, refine diagnostic skills of secondary complications, decrease the morbidity due to thrombosis and reduce the economic burden imposed on society by thrombosis.

Certain assays attempting to measure prothrombin activation through the measurement of F1.2 have been described in the literature. H. Lau (254 J. Biol. Chem. 8751–8761 (1979)) describes a radioimmunoassay for the quantification of prothrombin fragments F2/F1.2 using polyclonal antibodies to F2. These polyclonal antibodies do not completely distinguish between prothrombin and the fragments released by cleavage unless they undergo numerous immmunopurification steps.

EPA 0 303 983 ('983) describes a similar assay in which synthetic peptides corresponding to the carboxy-terminal end of F2/F1.2 were used to immunize animals to obtain polyclonal antisera to F2/F1.2. These antibodies also required immunopurification to function in immunoassays for the detection of F1.2.

The immunoassay taught by '983 coats a solid phase with the purified polyclonal antibody, which binds to epitopes on the carboxy terminus F1.2, and then introduces labeled polyclonal anti-prothrombin as the detection antibody. Although this assay has the ability to detect F1.2, the problems inherent in using polyclonals, including those of lowered specificity and difficulty in standardizing reagent lots are present in this assay. See also Pelzer, H., 18 Supp. 2 Haemostasis Abst. No. 102 (1988).

In the abstract, "Detection of Prothrombin Activation with Two-Site Enzyme Immunoassay for Fragment F1.2," by Shi, Q., 62 Thromb. Hemost. 165, Abst. No. 493 (1989), an immunogen and test assay similar to '983 are described. A polyclonal antibody to a synthetic peptide emulating the F1.2 carboxy terminus is used as the solid phase capture antibody and a labeled monoclonal anti-F1.2 is used for detection, most probably in the F1 region. Shi et al. states that immunoaffinity purification of the polyclonal capture antibody is not required. It is not known from the abstract if other purification methods are employed. Since the reagent is a polyclonal antibody, its specific availability is limited by the lifespan of the donor animal and is not reproducible.

Although solutions to the problems of detecting Antigens in order to measure prothrombin activation, to diagnose the formation of thrombotic conditions and to monitor the effects of anticoagulant therapy have been offered by the use of radio- and enzyme immunoassays detecting F1.2, the presently available tests are either cumbersome to use or not as sensitive or specific as needed by the clinician. One particular drawback inherent in all cited assays is the use of polyclonal antibodies as capture antibodies. Prothrombin, F1 and possibly other fragments in addition to F1.2 could be captured by these polyclonals, thereby decreasing the specificity of the test. Monoclonal antibodies to the Antigens and a new immunoassay utilizing these highly specific and sensitive monoclonal antibodies or the fragments thereof, are needed.

SUMMARY OF THE INVENTION

The present invention offers improved methods for assaying, in a sample, for prothrombin activation peptides F1.2 and F1.2.3 and their degradation forms des-R F1.2, F2 and des-R F2. In particular are claimed monoclonal antibodies and fragments thereof that have binding specificity for an epitope on the carboxy terminus on each of the Antigens. Also claimed are diagnostic kits for assaying, in a sample, for Antigens containing these monoclonal antibodies.

BRIEF DESCRIPTION OF THE DRAWINGS

FIG. 1A illustrates the activation of prothrombin in the coagulation cascade;

DETAILED DESCRIPTION OF THE INVENTION

Figure 1B:
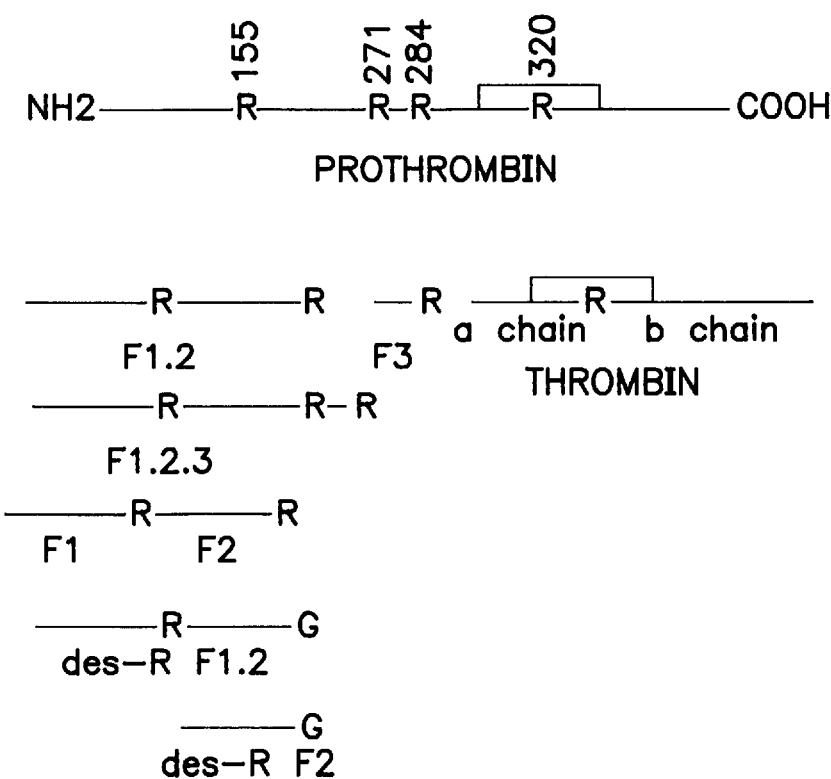
FIG. 1B illustrates prothrombin activation products and degradation forms.

The antibodies of the present invention are monoclonal antibodies specific to the carboxy terminus of the Antigens. In particular, a synthetic peptide based on the amino acid sequence of the appropriate Antigen was used as the hapten to raise these monoclonal antibodies.

A synthetic peptide is a chain of amino acids with a known sequence that are bound by peptide bonds, and can be prepared, for example, by chemical or recombinant means. The sequence can be the same as that of a particular native protein. Small synthetic peptides may be conjugated with appropriate carrier proteins to render them immunogenic. These conjugated peptides were used as immunogens in animals to raise monoclonal antibodies that bind to the Antigens' carboxy terminal epitopes, which are represented by the synthetic peptides.

The sequences used for the synthetic peptides in the present invention were derived from the cDNA sequence of prothrombin and prothrombin's known cleavage sites. In particular, the sequences of the terminal carboxy groups newly exposed upon cleavage were used. By using these sequences, we have developed and selected monoclonal antibodies having low, if any, crossreactivity with prothrombin.

One amino acid sequence of a synthetic peptide in the immunogenic conjugate that raises monoclonal antibodies to the carboxy terminus of F1.2, and therefore F2, contains at least Ile-Glu-Gly-Arg-OH. The most preferable synthetic peptide contains the sequence: Ser-Asp-Arg-Ala-Ile-Glu-Gly-Arg-OH. The carboxy terminal arginine as a carboxylic acid is a necessary component in this particular immunogen.

An amino acid sequence for a synthetic peptide used as an immunogen to produce monoclonal antibodies to the carboxy terminal of F1.2.3 has at a minimum, the sequence Phe-Asn-Pro-Arg-OH. The most preferred sequence is Tyr-Gln-Thr-Phe-Phe-Asn-Pro-Arg-OH. To produce monoclonal antibodies to the degradation fragments des-R F1.2 and des-R F2, the preferred sequence is Ser-Asp-Arg-Ala-Ile-Glu-Gly-OH.

These peptides can be produced using methods well known to those skilled in the art. Organic chemical methods for peptide synthesis include the coupling of amino acids using a condensation reaction, using either a homogeneous phase or a solid phase. Commonly known methods for condensation reactions include the carbodiimide method, the azide method, the mixed anhydride method and the method using activated esters, as described in *The Peptides, Analysis, Synthesis, Biology Vol.* 1–3 (E. Gross ed. 1979, 1980, 1981). The solid phase method is described by Merrifield, 85 J. Amer. Chem. Soc. 2149 (1963). Suitable peptides may also be purchased from suppliers such as Cambridge Research Biochemicals, Cambridge, UK or Multiple Peptide Systems, San Diego, Calif.

We conjugated the synthetic peptide of choice to a carrier molecule to produce an immunogen. Any effective carrier molecule may be used. Appropriate carrier molecules include, for example, ovalbumin, polysaccharide, marine keyhole limpet hemocyanin, and transferrin. The most preferred carrier for use in the present invention is ovalbumin.

Conjugation methods are known to those skilled in the art, and can involve the use of chemical crosslinking agents or oxidation reactions, as taught, for example by Peter, K., 46 Ann. Rev. Biochem. 523–51 (1977). We prepared conjugates of the synthetic peptide and a carrier protein using the crosslinking agent N-succinimidyl 3-(2-pyridyldithio) propionate (SPDP) and the basic method of Carlsson, J., 173 Biochem J. 723–737 (1978).

A modification of the immunization procedure in mice described by M. Cianfriglia, et al., 2(4) Hybridoma 451–457 (1983), produced the relevant anti-Antigen monoclonal antibodies. The modification was necessary because five previous fusion attempts using other immunization protocols did not generate the appropriate IgG monoclonal antibodies specific for the immunogen. However, serum from the immunized mice that did not produce the relevant monoclonal antibodies did contain highly reactive and specific polyclonal antibodies to the Antigens.

Mice were immunized by an intraperitoneal (I.P.) injection of the conjugated synthetic peptide in complete Freund's adjuvant. Following priming, the mice were rested for 21 days and then boosted with the same immunogen in incomplete Fruend's adjuvant. Final boosts were conducted on days 25, 26 and 27, using the same immunogen in PBS by both the intravenous (I.V.) and I.P. routes. Although mice are the preferred vehicle, other animals, such as rats and guinea pigs, can also be used.

The immunized mice were sacrificed on day 28 and spleen cells were removed. Following a modified method (B. Butman, et al., 54 Appl. Env. Micro. 1564–1569 (1983)) of Kohler and Milstein, 256 Nature 495 (1975), the cells were fused with a non-secretor plasma cell line (P3X63Ag8.653, ATCC Number CRL 1580, Rockville, Md.) to produce hybridomas, and distributed into microtiter trays containing Iscove's Modified Dulbecco's medium plus hypoxanthine, aminopterin, and thymidine (HAT), and either 20% equine serum or 5% fetal bovine serum, 1% Nutridoma (Boehringer Mannheim), and peritoneal mononuclear feeder cells. Supernatants were screened for anti-Antigen antibody by an indirect enzyme-linked immunoassay ("ELISA") and selected positive hybridoma cultures were cloned.

Screening of the hybridomas for production of the appropriate antibody is an integral step in this invention. For example, in screening for a monoclonal antibody to F1.2, the monoclonal antibody should be nonreactive, or at the least, should only minimally crossreact, with prothrombin or F1. It must also recognize the epitope on native F1.2 and F2, and not just the synthetically produced peptide used for immunization.

Screening assays revealed that forty-four monoclonal antibodies derived from the selected positive hybridomas displayed the desired specificity described above.

Eight hybridomas were cloned and six selected clones were propagated as ascites tumors in mice, using standard methods. Other methods for propagating monoclonal antibodies are known to those skilled in the art, including growth in bioreactors such as hollow fiber cartridges or fermenters. Any antibodies propagated using these methods would also need to undergo characterization. Monoclonal antibodies in ascites were characterized by ELISA to confirm the specificity demonstrated in culture by the six cloned hybridomas. Antibodies were purified from these ascites fluids using Protein A affinity chromatography. Other methods of immunopurification known to those skilled in the art may also be used.

The purified anti-Antigen monoclonal antibodies were characterized for isotype and isoelectric point. Immunochemical analyses were conducted to determine monoclonal antibody specificity using ELISA. All six antibodies were found to specifically bind to the following antigens: F1.2, F2, and PF2-OVA. PF2-OVA designates a conjugate of the synthetic peptide emulating the F1.2 carboxy terminal with ovalbumin. No specific binding was observed for any of the antibodies against the following antigens: prothrombin, thrombin, F1, des-R-PF2-OVA, ovalbumin. Des-R-PF2-OVA designates a conjugate of ovalbumin with a synthetic peptide emulating the carboxyl terminal of des-R F1.2.

These anti-Antigen monoclonal antibodies, and fragments thereof, can be used in a variety of immunoassays to detect Antigen. A preferred method to assay for Antigen incorporates at least one anti-Antigen monoclonal antibody and at least one labeled analyte, which can be a labeled antibody or a labeled peptide, preferably an anti-Antigen antibody, and most preferably, a polyclonal antibody, in a sandwich immunoassay comprising:

a) coat solid phase with the anti-Antigen monoclonal antibody,
b) add sample to the coated solid phase and incubate,
c) wash the solid phase,
d) add labeled anti-Antigen antibody and incubate,
e) wash the solid phase,
f) detect label activity, and
g) read reaction.

The labeled antibody may have biding specificity for the antibody on the solid phase or the Antigen. The sample is preferably plasma, but other body fluids such as serum, whole blood, urine, cerebral spinal fluid and synovial fluid may be used. The wash solution is generally a buffered solution, but may be water or may contain other components. The label is preferably horseradish peroxidase for the enzyme system, but other enzymes such as alkaline phosphatase, glucose-6-phosphate dehydrogenase, luciferase and beta-galactosidase may be used, as known by those skilled in the art. Examples of labels useful in non-enzyme systems include fluorescent labels, such as fluoroisothiocyanate, rhodamine or fluorescein, radioisotopes for radioimmunoassays, and particles.

Other methods for the in-vitro detection of Antigens, which are provided as examples but are not intended to be limiting, include competitive inhibition assays, single step assays, and agglutination assays.

The present invention includes diagnostic test kits to be used in assaying for Antigens in samples, comprising at least one anti-Antigen monoclonal antibody which is substantially nonreactive to prothrombin. In addition, diagnostic kits may contain buffer solutions, labeled polyclonal or monoclonal anti-Antigen antibodies, antigens or peptides and any accessories necessary for the use of the kit.

The following examples describe the production and use of anti-F1.2 monoclonal antibodies. These examples are given merely for illustration of the present invention and are not to be construed as a limitation on the remainder of the specification in any way.

EXAMPLE I.

Preparation of Synthetic Peptides

The amino acid sequences of synthetic peptides used in preparation of the immunoconjugate and for screening and characterizing anti-F1.2 antibodies are shown in Table 1.

TABLE 1

SEQUENCES** OF SYNTHETIC PEPTIDES AND PARTIAL SEQUENCES OF F1.2 AND PROTHROMBIN

| Peptide | # Amino Acids | Sequence* |
|---------|---------------|-----------|
| PF2     | 10 (8 + 2)    | c g S D R A I E G R |
| desRPF2 | 9 (7 + 2)     | c g S D R A I E G |
| XPF2    | 10 (8 + 2)    | c g A I E G R T A T S |
| PF2.14  | 14 (12 + 2)c g L D E D S D R A I E G R |
| PF2.K   | 8             | S D R A I E G K |
| PF2.NH2 | 8             | S D R A I E G R-amide |
| PF2.8   | 8             | S D R A I E G R |
| PF2.6   | 6             | R A I E G R |
| PF2.5   | 5             | A I E G R |
| PF2.4   | 4             | I E G R |
| PF2.3   | 3             | E G R |

Native Protein

| F1.2        | 271 | ...L D E D S D R A I E G R |
| Prothrombin | 530 | ...L D E D S D R A I E G R T A T... |

*All synthetic peptides have a free carboxyl group at the C-terminal with exception of PF2.NH2 which has an amidated carboxyl terminal (—CONH$_2$). Four peptides have the amino acids C and G at their N-termini for conjugation purposes only.
**Symbols = A (alanine), R (arginine), D (aspartic acid), C (cysteine), E (glutamic acid), G (glycine), I (isoleucine), L (leucine), K (lysine), S (serine), T (threonine)

Peptides designated PF2, desRPF2, XPF2, and PF2.14 were purchased from Cambridge Research Biochemicals, Cambridge, UK; remaining peptides were purchased from Multiple Peptide Systems, San Diego, Calif. The sequence of peptide PF2, Cys-Gly-Ser-Asp-Arg-Ala-Ile-Glu-Gly-Arg-OH, is based on the last eight amino acids of the F1.2 carboxyl terminus, -Ser-Asp-Arg-Ala-Ile-Glu-Gly-Arg-OH, plus an additional two amino acids, cysteine and glycine, useful for conjugation purposes. Peptides desRPF2, XPF2 and PF2.14 also include (CG) at their N-termini for conjugation purposes.

Example II

Preparation of Immunoconjugate

PF2 as described in Example I above and ovalbumin were coupled using the heterobifunctional crosslinking agent N-succinimidyl 3-(2-pyridyldithio)propionate (SPDP).

For the coupling procedure, an ethanolic solution of SPDP was prepared, and the concentration of active ester was determined using the method of Carlsson (See above). Ovalbumin (Grade V; Sigma Chemical Co.) was dissolved in coupling buffer of 100 mM NaCl, 100 mM NaHPO$_4$, 0.02% NaN$_3$, pH 7.5, then gel filtered on Sephadex G-25™ (Pharmacia LKB Biotechnology, Inc.) equilibrated in coupling buffer. Ovalbumin was incubated with a 17-fold molar excess of SPDP for 30 min at room temperature, then gel filtered as above. The extent of ovalbumin thiolation was estimated to be 12.5 moles pyridyldisulfide groups/moles ovalbumin, by reducing the thiolated material with dithiothreitol and monitoring at 343 nm the release of pyridylthione. The N-terminal cysteine sulfhydryl group of PF2 was reduced by incubating 1 mM PF2 in coupling buffer with 50 mM dithiothreitol for 10 minutes at room temperature. PF2 was quickly gel filtered on Sephadex G-10™ (Pharmacia LKB Biotechnology, Inc.) equilibrated in coupling buffer then incubated at room temperature with thiolated ovalbumin at a 1.25 molar excess of PF2 relative to ovalbumin's pyridyldisulfide sites. The coupling reaction was monitored spectrophotometrically by the release of pyridylthione which has an absorbance maximum at 343 nm and a known extinction coefficient (8.08 ml/μmol). Coupling was completed within 10 min, and average loading was 8.9 mol PF2/mol ovalbumin. The conjugate identified as PF2-OVA was stored at −20° C. prior to use as immunogen.

Example III
Preparation of Other Peptide-Containing Conjugates

Conjugates of ovalbumin with desRPF2 or XPF2, and horseradish peroxidase (HRP; Sigma Chemical Co.) with PF2.14 were prepared using SPDP as crosslinking agent as described in Example II above. For the pyridyldisulfidation reactions, SPDP was incubated at room temperature for 75 minutes with HRP at a 0.83:1 molar ratio, or with ovalbumin at a 30:1 molar ratio. Average final loading was 10.2 moles des-RPF2/mole ovalbumin, 7.4 moles XPF2/mole ovalbumin, and 1.6 mole PF2.14/HRP. Conjugates were stored at −20° C. until used in screening and characterizing antibodies.

Example IV
Preparation of Proteins for Screening and Characterizing Antipeptide Monoclonal Antibodies F1.2, F2, and prothrombin must be carefully purified to homogeneity in order to eliminate error in screening for anti-peptide antibodies in culture fluids. Often prothrombin contains contaminants such as F1 and F2 which can interfere in screening for and evaluating anti-peptide antibodies. Since the desired antibodies must not recognize prothrombin, it is important that prothrombin be free of F1.2 and F2.

Low levels of contaminants were removed from commercially available prothrombin (Enzyme Research Inc.) with a heparin Sepharose™-column (Pharmacia LBK Biotechnology, Inc). This was done by dialyzing 12 mg of prothrombin vs a 20 mM tris, 50 mM NaCl, pH 7.5 buffer overnight at 4 deg C. and later slowly passing through a 2.6×29 cm heparin Sepharose™ column equilibrated in the same buffer (See Lau above). Purified prothrombin displayed a single band on reduced and non-reduced silver stained sodium dodecyl sulfate polyacrylamide gel electrophoresis ("SDS-PAGE").

Crude F1.2 was generated when catalytic amounts of purified factor Xa (Boehringer Mannheim) were allowed to react with 25 mg of purified prothrombin in the presence of 5 μM Thromstop™ (American Diagnostica Inc.) (NAPAP, N-alpha-(2-naphthysulfononylglycyl)-D,1-amidino-phenylalanin-piperidide) and 100 mM $CaCl_2$. The progress of the reaction was monitored by SDS-PAGE and terminated by irreversibly inhibiting factor Xa and thrombin with GGACK™ (Calbiochem Corp.) (dansyl-L-glutamyl-glysyl-L-arginine chloromethyl ketone), and PPACK™ (Calbiochem Corp.) (D-phenylalanyl-L-prolyl-L-arginine chloromethyl ketone), 50 μM final each. Both the Thromstop™ and the high level of $CaCl_2$ are necessary to stop the thrombin produced in the generation of F1.2 from inactivating prothrombin or destroying F1.2. PPACK™ cannot be used to replace Thromstop™ because it will inhibit factor Xa in addition to the desired thrombin.

The F1.2 generated above was purified by first dialyzing it against a 20 mM tris, 50 mM NaCl, pH 7.4 buffer solution overnight at 4 deg C. and was applied to a 2.6×29 cm heparin Sepharose™ column using the conditions described above for the purification of prothrombin. The peak containing F1.2 was identified by SDS-PAGE and subsequently applied to a Mono-Q™ Pharmacia LBK Biotechnology, Inc., HR 5/5 fast protein liquid chromatography (FPLC) column that was equilibrated in the buffer solution. Purified F1.2 was eluted as the last peak in a 50 minute NaCl gradient (50 mM NaCl to 500 mM NaCl in 20 mM tris, pH 7.4). The F1.2 was greater than 95% pure based on Coomassie blue stained SDS-PAGE and had an apparent molecular weight of 43,000 daltons. The minor contaminants included F1 and occasionally prothrombin.

Crude F1 and F2 were generated by allowing the protease (s) from *Oxyuraneous venom* (approx. 0.1 mg; Sigma Chemical Co.) to cleave prothrombin ($^{18}85$ mg) into F1, F2, and thrombin. The progress of the reaction was monitored by watching the increase in thrombin activity with a thrombin-sensitive chromostrate. The incubation was terminated after 60 minutes by adding PPACK™ and GGACK™ at a final concentration of 50 μM each. Both F1 and F2 were subsequently purified on a Mono-Q™ column as described above for purification of F1.2.

Example V
Immunization Protocol

BALB/c mice were immunized with PF2-OVA immunoconjugate as described in Example II above, using a modification of the Cianfriglia procedure. Mice were primed on day 1 with 50 μg immunogen in complete Freund's adjuvant I.P., and rested for 21 days. On day 22, mice were boosted with 50 μg immunoconjugate in incomplete Freund's adjuvant and then final boosts were administered on days 25, 26, and 27 using 5 μg immunoconjugate in phosphate buffered saline (PBS), delivered both I.P. and I.V. On day 28 the spleen was removed and splenocytes were isolated for hybridoma fusion.

Example VI
Preparation of Hybridomas

Immune splenocytes were fused to P3X63Ag8.653 mouse myeloma cells by a modification, described in Butman above, of the technique described by Kohler and Milstein. "Fusion 97" cells were plated into Iscove's Modified Dulbecco's Medium containing 20% equine serum and HAT, and "Fusion 98" cells were plated into Iscove's Modified Dulbecco's Medium containing 1% Nutridoma™ (Boehringer Mannheim), 5% fetal bovine serum and HAT over a feeder layer of mouse peritoneal exudate cells. Cultures were fed every two to three days by replacing 50% of the medium in each culture well with fresh medium.

Example VII
Screening Antibodies

Cultures exhibiting hybridoma growth in HAT medium were screened by ELISA for the production of monoclonal antibodies reactive with F1.2. For this purpose, 100 μl/well of purified F1.2 (5 μg/ml) was coated overnight in PBS, pH 7.0, on Immulon II™ microtitration plates (Dynatech, Va.) and then blocked with a solution of PBS containing 3% Fish gelatin (300 μl/well). Hybridoma supernatants (100 μl/well) were then added and incubated for 60 minutes at 37° C., followed by washing 5 times with deionized water containing 0.5% glycerol and 0.05% Tween 20™ (Rohm and Haas) to remove unbound antibodies. Specific antibody binding was detected using 100 μl/well of HRP-conjugated goat antibodies to mouse immunoglobulin (IgG plus IgM) for 60 minutes, washed, and then developed with 100 μl/well of tetramethylbenzidine chromogenic substrate for 30 minutes. The reaction was stopped using 100 μl/well of 2N $H_2SO_4$ and read using an automated microplate reader at 450 nm. Positive wells were then expanded and retested for specificity by ELISA against F1.2, PF2-OVA, OVA, and prothrombin. Fusion 97 yielded 13 out of 213 F1.2 specific hybridomas and Fusion 98 yielded 31 out of 635 F1.2 specific hybridomas. Isotype determination was conducted on supernatants using a commercial double immunodiffusion kit. A total of eight hybridomas from Fusion 97 and Fusion 98 were chosen for cloning based upon specificity data and IgG isotype.

EXAMPLE VIII
Cloning and Scale-Up of Hybridomas

Hybridomas were cloned by two rounds of limiting dilution cloning into their respective aminopterin-free hybridoma culture medium containing 50% L929 conditioned medium. The latter was prepared by growth of a confluent monolayer of L929 murine fibroblasts, obtained from ATCC in Iscove's Modified Dulbecco's medium containing 10% fetal bovine serum for three to four days, followed by centrifugation and filter sterilization of the conditioned medium. Three stable hybridoma clones from each of the 2 fusions were propagated as ascites tumors in Pristane® (Aldrich Chemical Co.)-primed CD2 F1 mice (BALB/c x DBA F1 hybrid) following conventional protocols.

Six IgG monoclonal antibodies were purified from ascites by affinity chromatography using protein A Sepharose™.

EXAMPLE IX

Characterization of Monoclonal Antibodies in Ascites Fluid

Figure 2:
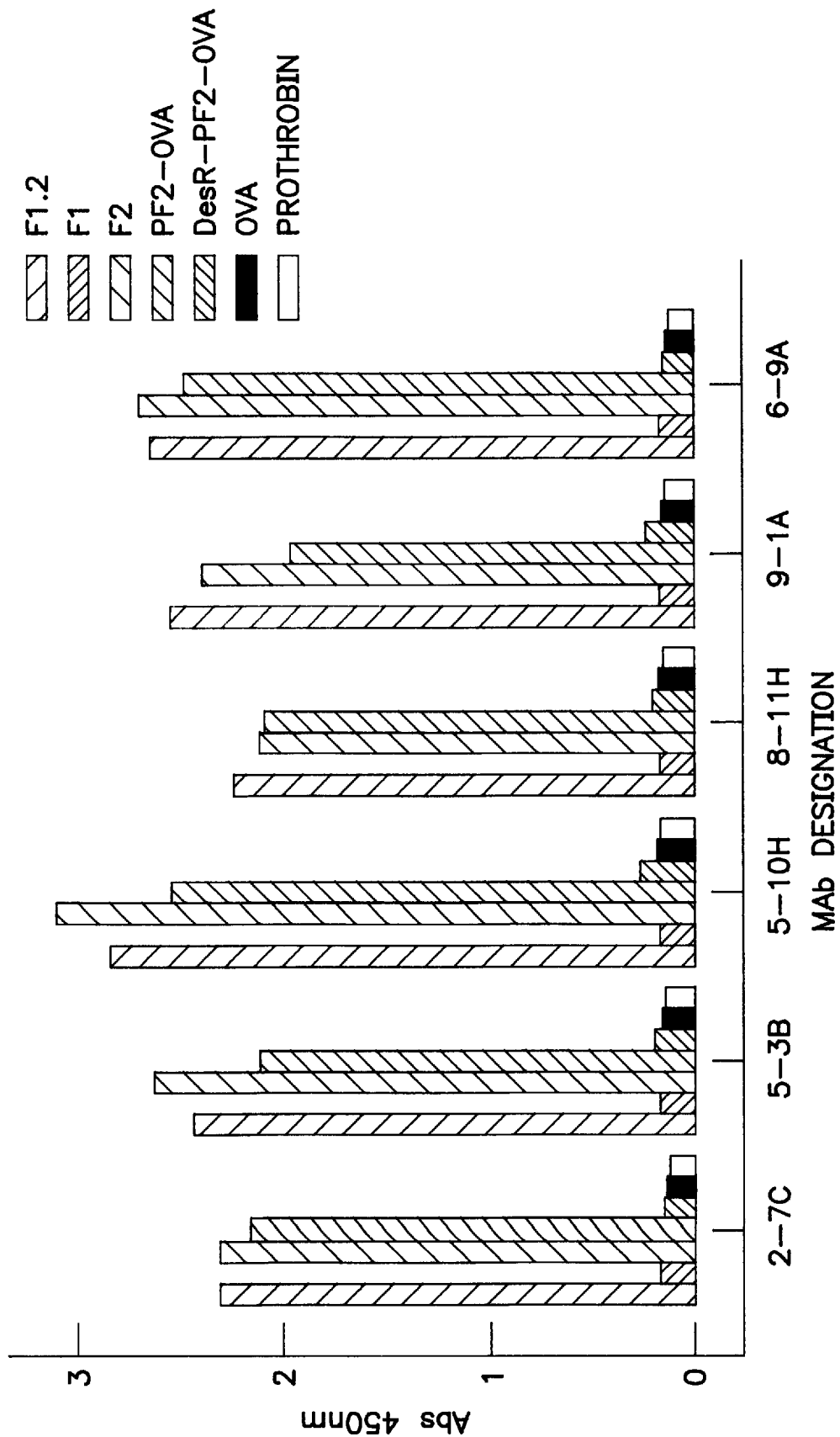
FIG. 2 is a graph showing the ELISA characterization of anti-PF2 Mab in Ascites where ELISA reactivity profiles are shown against eight antigens.

Monoclonal antibodies in ascites fluids were confirmed for specificity by ELISA as described in Example VII above, using the following antigens coated onto Immulon II™ microtitration wells: F1.2, F1, F2, PF2-OVA, OVA, des-R-PF2-OVA and prothrombin. The results are summarized in Table 2 and FIG. 2. All six monoclonal antibodies showed similar ELISA reactivity profiles against the eight antigens tested. Positive reactivity was seen against F1.2, R2 and PF2-OVA. Negative reactivity was seen with F1, des-R-PF2-OVA, OVA, prothrombin and thrombin.

TABLE 2

ELISA Characterization of PF2 Specific Monoclonal Antibodies from ASCITES

| MAb Designation | MAb Isotype | Ascites Dilution | F1.2 | F1 | F2 | PF2-OVA | desRPF2OVA | OVA | Prothrombin | Thrombin |
|---|---|---|---|---|---|---|---|---|---|---|
| F98/2-7C.6B | IgG1 | $10^{-3}$ | 2.295 | 0.155 | 2.297 | 2.150 | 0.143 | 0.134 | 0.127 | 0.128 |
|  |  | $10^{-4}$ | 2.116 | 0.154 | 1.924 | 1.936 | 0.134 | 0.127 | 0.126 | 0.126 |
|  |  | $10^{-5}$ | 0.807 | 0.144 | 0.741 | 0.641 | 0.128 | 0.124 | 0.128 | 0.124 |
| F98/5-3B.2C | IgG1 | $10^{-3}$ | 2.419 | 0.149 | 2.616 | 2.099 | 0.186 | 0.146 | 0.141 | 0.144 |
|  |  | $10^{-4}$ | 2.211 | 0.140 | 2.117 | 2.107 | 0.151 | 0.137 | 0.142 | 0.145 |
|  |  | $10^{-5}$ | 0.767 | 0.150 | 0.740 | 0.719 | 0.147 | 0.138 | 0.137 | 0.131 |
| F98/5-10H.7G | IgG2b | $10^{-3}$ | 2.823 | 0.164 | 3.089 | 2.523 | 0.254 | 0.158 | 0.151 | 0.147 |
|  |  | $10^{-4}$ | 2.529 | 0.148 | 2.492 | 2.517 | 0.246 | 0.150 | 0.141 | 0.139 |
|  |  | $10^{-5}$ | 1.057 | 0.159 | 0.935 | 0.941 | 0.185 | 0.152 | 0.149 | 0.145 |
| F97/8-11H.2C | IgG1 | $10^{-3}$ | 2.228 | 0.169 | 2.078 | 2.061 | 0.185 | 0.154 | 0.136 | 0.131 |
|  |  | $10^{-4}$ | 2.445 | 0.149 | 2.364 | 2.050 | 0.154 | 0.133 | 0.130 | 0.120 |
|  |  | $10^{-5}$ | 1.304 | 0.141 | 1.220 | 1.052 | 0.133 | 0.135 | 0.129 | 0.123 |
| F97/9-1A.6B | IgG1 | $10^{-3}$ | 2.522 | 0.151 | 2.362 | 1.941 | 0.213 | 0.142 | 0.127 | 0.123 |
|  |  | $10^{-4}$ | 1.815 | 0.135 | 1.682 | 1.521 | 0.164 | 0.136 | 0.126 | 0.121 |
|  |  | $10^{-5}$ | 0.584 | 0.133 | 0.516 | 0.416 | 0.143 | 0.132 | 0.128 | 0.118 |
| F97/6-9A.2C | IgG1 | $10^{-3}$ | 2.621 | 0.134 | 2.673 | 2.450 | 0.145 | 0.141 | 0.131 | 0.118 |
|  |  | $10^{-4}$ | 2.233 | 0.134 | 2.226 | 2.034 | 0.142 | 0.144 | 0.132 | 0.121 |
|  |  | $10^{-5}$ | 0.942 | 0.140 | 0.847 | 0.731 | 0.144 | 0.156 | 0.136 | 0.123 |

X. Characterization of Purified Monoclonal Antibodies

Six purified monoclonal anti-F1.2 antibodies were characterized in terms of physical properties and specificity.

a) Physical Properties i) Table 3 lists the physical characteristics of the monoclonal antibodies, including isotype, isoelectric points (pI), and amount required to saturate microtiter wells. Antibody isotype was determined as described in Example VII above. Isoelectric points were established by isoelectric focusing using the Pharmacia LKB Biotechnology, Inc. Phast-Gel Systems™. Banding patterns were consistent with the presence of monoclonal, not polyclonal, antibodies.

TABLE 3

Properties of Purified Anti-F1.2 Monoclonal Antibodies

| MoAB | Isotype | pI | μg MoAB for Well Saturation | MoAB Titer vs. PF2-OVA(ng/ml) | Background A450 with 5 μg/ml MoAB | Reactivity at 5 μg/ml MoAB (+ = > A450 > 3X Background A450) | | | | | | | | |
|---|---|---|---|---|---|---|---|---|---|---|---|---|---|---|
| | | | | | | F1.2 | F1 | F2 | II | IIa | des-R PF2-OVA | XPF2-OVA | PcPr-OVA | Pyr-OVA |
| Fusion F97 | | | | | | | | | | | | | | |
| 6-9A | IgG$_1$ | 6.0–6.6 | 0.65 | >8000 | 0.035 | + | − | + | − | − | − | − | − | − |
| 8-11H | IgG$_1$ | 6.4–6.8 | 0.51 | 100 | 0.040 | + | − | + | − | − | − | − | − | − |
| 9-1A | IgG$_1$ | 6.4–6.8 | 0.67 | 6 | 0.045 | + | − | + | − | − | − | − | − | − |
| Fusion F98 | | | | | | | | | | | | | | |
| 2-7C | IgG$_1$ | 6.5–7.0 | 0.54 | 20 | 0.040 | + | − | + | − | − | − | − | − | − |
| 5-3B | IgG$_1$ | 6.6–7.0 | 0.56 | 23 | 0.048 | + | − | + | − | − | − | − | − | − |
| 5-10H | IgG$_{2b}$ | >8 | 0.52 | 12 | 0.081 | + | − | + | − | − | − | − | + | − | ii) To determine the amount of antibody required to saturate a microtiter well, 100 μL antibody between 5 pg/mL and 90 μg/mL in a 150 mM NaCl, 20 mM tris, 5 mM CaCl$_2$, pH 7.4 buffer, was incubated with Griener™ microtiter wells (Organon Teknika, Inc.) at room temperature for 18 hours. The wells were washed three times with 300 uL/well of a 150 mM NaCl, 0.05% Tween-20™ solution, then blocked with 200 uL of 150 mM NaCl, 20 mM tris, 5 mM CaCl$_2$, 5% non-fat dry milk, pH 8.2, for one hour at 37° C., then washed as above. HRP-labeled goat anti-mouse immunoglobulin, from Boehringer Mannheim, was incubated with each well for one hour at 37° C. Wells were washed as above, and HRP activity was measured at 450 nm using tetramethylbenzidine/hydrogen peroxide as indicator, sulfuric acid as stop solution, and a 10 minute color development time. The monoclonal antibody concentration at which HRP activity no longer increased was considered the concentration required for well saturation. For the six monoclonal antibodies, well saturation occurred at antibody amounts consistent with that routinely reported for monoclonal antibodies.

iii) Specificity. Table 3 summarizes the specificity of the purified anti-F1.2 antibodies with respect to F1.2, F1, F2, prothrombin, thrombin, the ovalbumin-PF2 immunoconjugate, ovalbumin conjugates with desRPF2, XPF2, and an unrelated peptide (PCPr), and pyridyldisulfidated ovalbumin.

Figure 3:
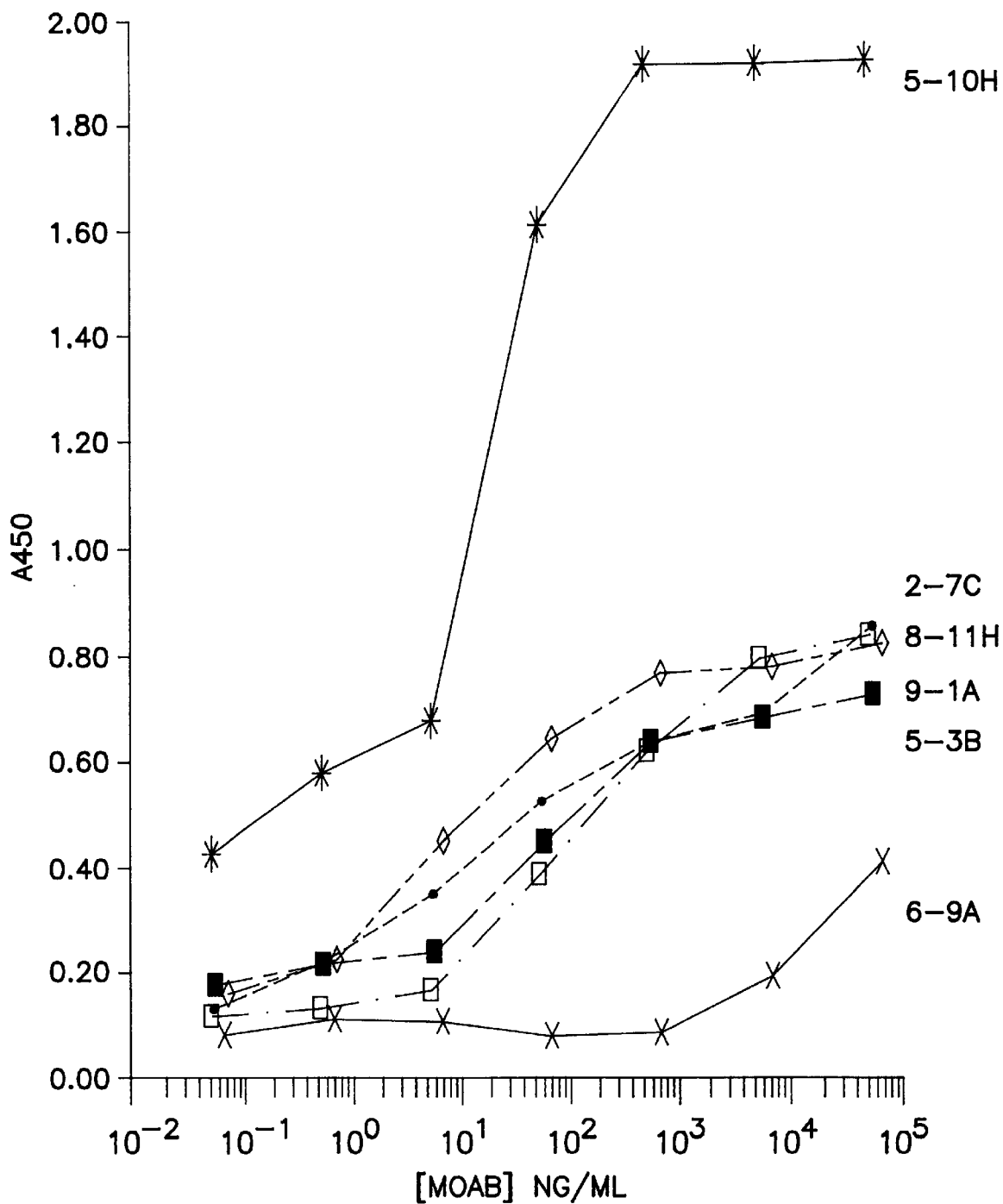
FIG. 3 illustrates the titre for each of six antibodies, which titre is the midpoint of the binding isotherm with plate-bound ovalbumin-PF2 conjugate where reactivity is defined as an absorbance at 450 nm greater than three times that of the background when 5 mg per ml antibody is used.

For use in these studies, Griener™ microtitration plates were coated with antigen (1 μg thrombin; 100 ng each of F1.2, F1, F2, prothrombin, ovalbumin-PCPr, and pyridyldisulfidated ovalbumin; 10 ng each of ovalbumin conjugates with PF2, desRPF2, and XPF2) in 150 mM NaCl, 20 mM tris, 5 mM CaCl$_2$, pH 8.2, for 18 hours at room temperature. Plates were then washed and blocked as described above. Monoclonal antibody (100 uL of 50 pg/mL to 70 μg/mL antibody in a 150 mM NaCl, 20 mM tris, 5 mM CaCl$_2$, 0.02% Tween-20™, pH 7.4 buffer) was incubated with the coated plates for one hour at 37° C. Each plate was washed as above, and bound antibody detected using HRP-labeled goat anti-mouse IgG (H+L) as described above. The titer for each antibody was the midpoint of the binding isotherm with plate-bound ovalbumin-PF2 conjugate. (See FIG. 3.) Reactivity was defined as an absorbance at 450 nm greater than three times that of the background when 5 μg/mL antibody was used.

Each of the six monoclonal antibodies recognized F1.2 and F2 and, with exception of 5-10H, failed to recognize F1, prothrombin (II), thrombin (IIa), pyridyldisulfidated ovalbumin (pyr-OVA), or conjugates of ovalbumin with des-R-PF2, XPF2, and PCPr. Monoclonal antibody 5–10H exhibited higher background than the other five monoclonal antibodies, probably due to nonspecific interactions. When an even stricter definition of reactivity was applied, (A450 greater than background using 50 μg/mL antibody), antibodies 6–9A, 8–11H, 9–1A, 2–7C, and 5–3B still failed to recognize F1, prothrombin, thrombin, or any ovalbumin conjugates tested.

iv) The antibodies were also evaluated for ability to capture F1.2 from solution in a sandwich ELISA format. Antibody-coated Griener™ plates were prepared and blocked as described above for the plate saturation study; concentrations of antibody known to saturate the plate were used. Various concentrations of F1.2 (0.023–23M) in a 150 mM NaCl, 20 mM tris, 5 mM CaCl$_2$, pH 7.5 solution, were incubated in the plate wells for 1 hour at 37° C. then unbound F1.2 was removed by washing as above. HRP-labeled polyclonal antibodies to the prothrombin calcium-dependent conformer (See Example XI) were incubated with the plate for one hour at 37° C., after which the plate was washed. HRP activity was determined as previously described.

Figure 4:
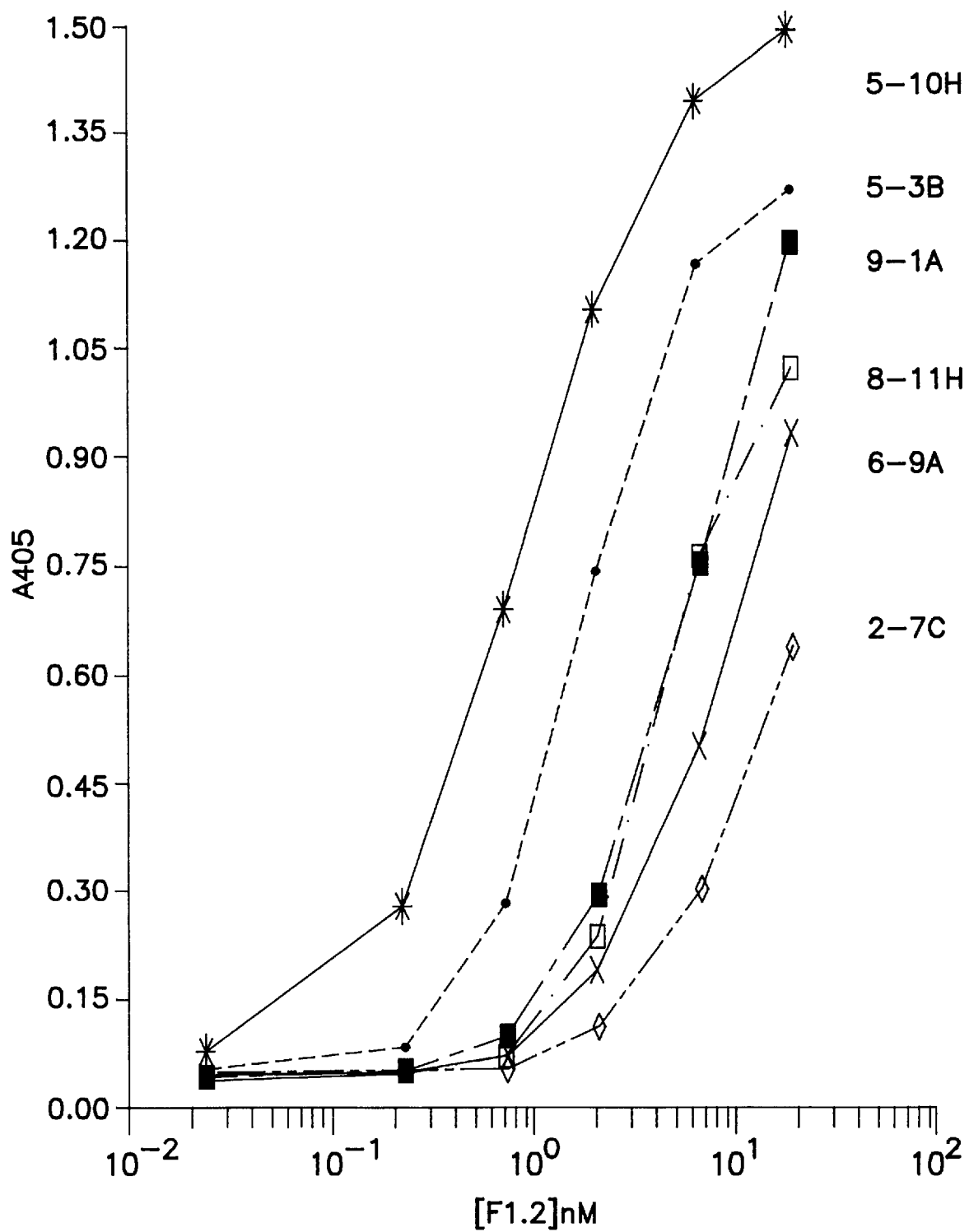
FIG. 4 illustrates the F1.2 binding isotherms for each of the six monoclonal antibodies.

The F1.2 binding isotherms for the monoclonal antibodies are shown in FIG. 4. Each antibody was able to bind solution-phase F1.2 and could have been used for development of an F1.2 sandwich ELISA. Antibodies 5–10H and 5–3B were superior in terms of detecting the lowest concentration of F1.2. Due to the nonspecific binding properties shown by 5–10H, 5–3B was selected as the antibody of choice for development of an F1.2 ELISA and deposited at the American Type Culture Collection located at 12301 Parklawn Drive, Rockville, Md. 20852, USA, on Nov. 2, 1989 and given the number ATCC HB10291.

v) Additional specificity studies were performed to better define the epitope requirements of monoclonal antibody 5–3B. A competitive ELISA format was used which employed microtitration plates coated as described above with saturating concentration of 5–3B. HRP-labeled PF2.14 (50 μL of 10 nM conjugate) was incubated for 75 min at 37° C. with an equal volume of various concentrations of purified F1.2 or synthetic peptide in the presence of a 150 mM NaCl, 20 mM tris, 5 mM CaCl$_2$, 0.05% Tween-20™, pH 7.2 buffer solution. Wells were washed four times with 300 μL of a 150 mM NaCl, 20 mM tris, 0.05% Tween-20™, pH 7.2 buffer solution. HRP activity was determined as detailed above and reflected extent of HRP-PF2.14 binding (B). In the absence of competing antigen, maximal binding ($B_o$) was observed. The ratio of B/Bo reflected the percent binding for HRP-PF2.14.

Figure 5:
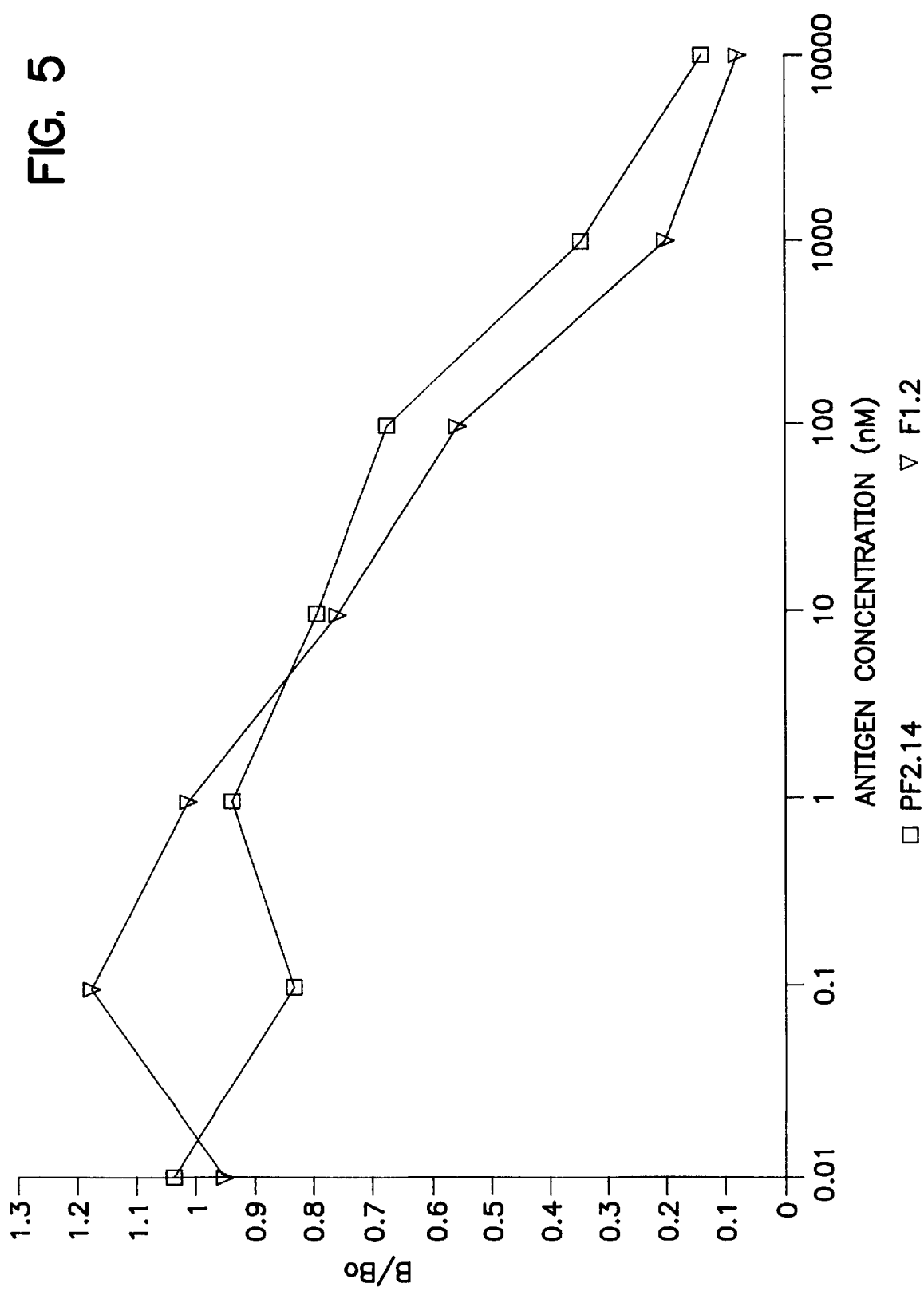
FIG. 5 illustrates the competition of F1.2 and PF2.14 with HRP-PF2.14 and confirms the ability of monoclonal antibody 5-3B to recognize both native protein and synthetic peptide.
Figure 6:
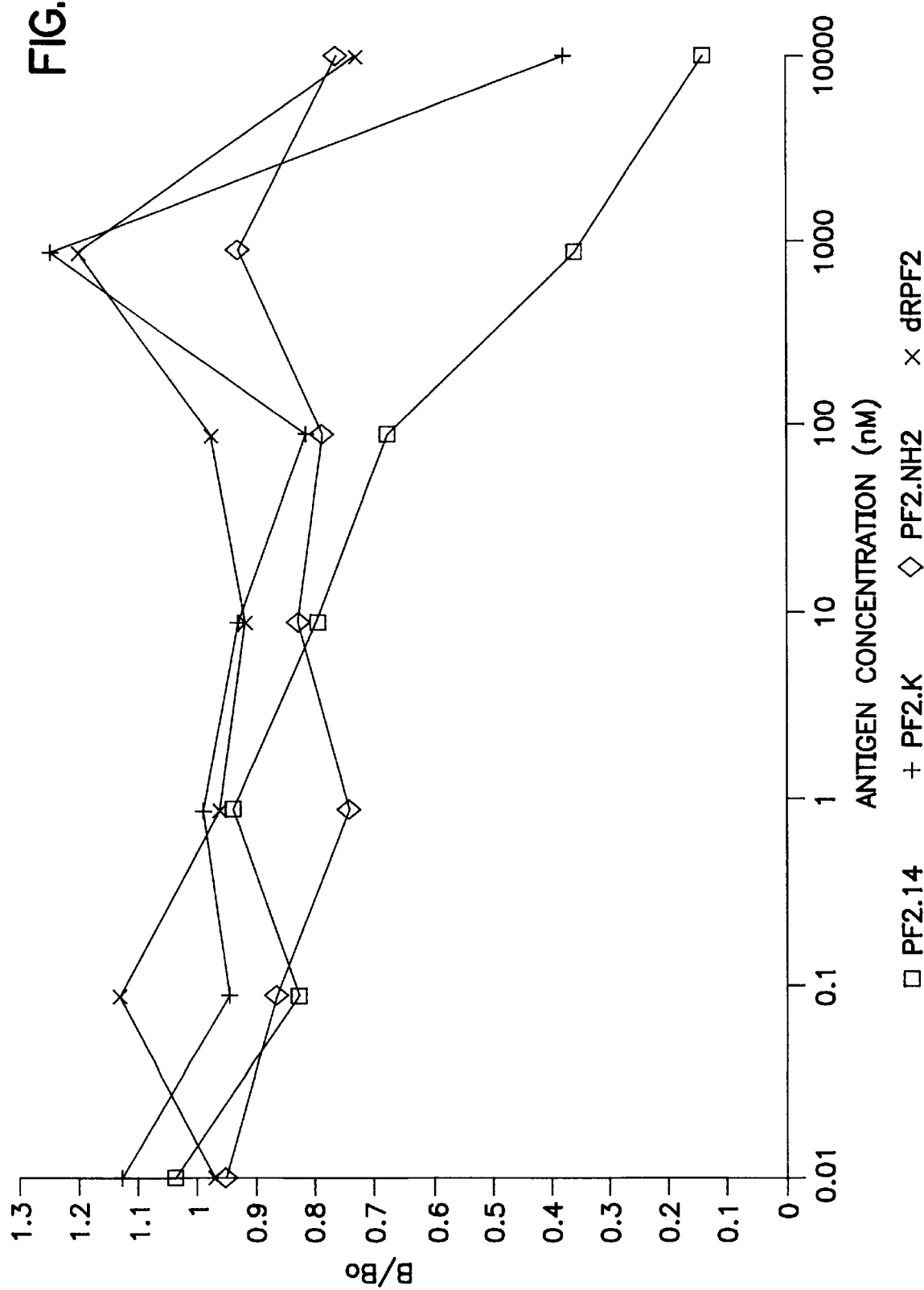
FIG. 6 illustrates that neither DES-RPF2 nor PF2.NH2 competes with HRP-PF2.14, and that PF2.K competes only at high concentration.

Both F1.2 and PF2.14 effectively competed with HRP-PF2.14 (FIG. 5), indicating the feasibility of a competitive assay format using labeled peptide and confirming the ability of 5–3B to recognize both native protein and synthetic peptide. In comparison, neither des-RPF2 nor PF2.NH2 competed with HRP-PF2.14, and PF2.K competed only at high concentration (FIG. 6). These results suggest that for an epitope to be recognized by 5–3B neither the presence of any C-terminal amino acid with a free carboxyl group nor a C-terminal arginine without a free carboxyl group is sufficient and that the presence of a C-terminal positively-charged amino acid (i.e., lysine) with a free carboxyl group is important but not sufficient. Optimum recognition occurs when a C-terminal arginine with a free carboxyl group is present.

Figure 7:
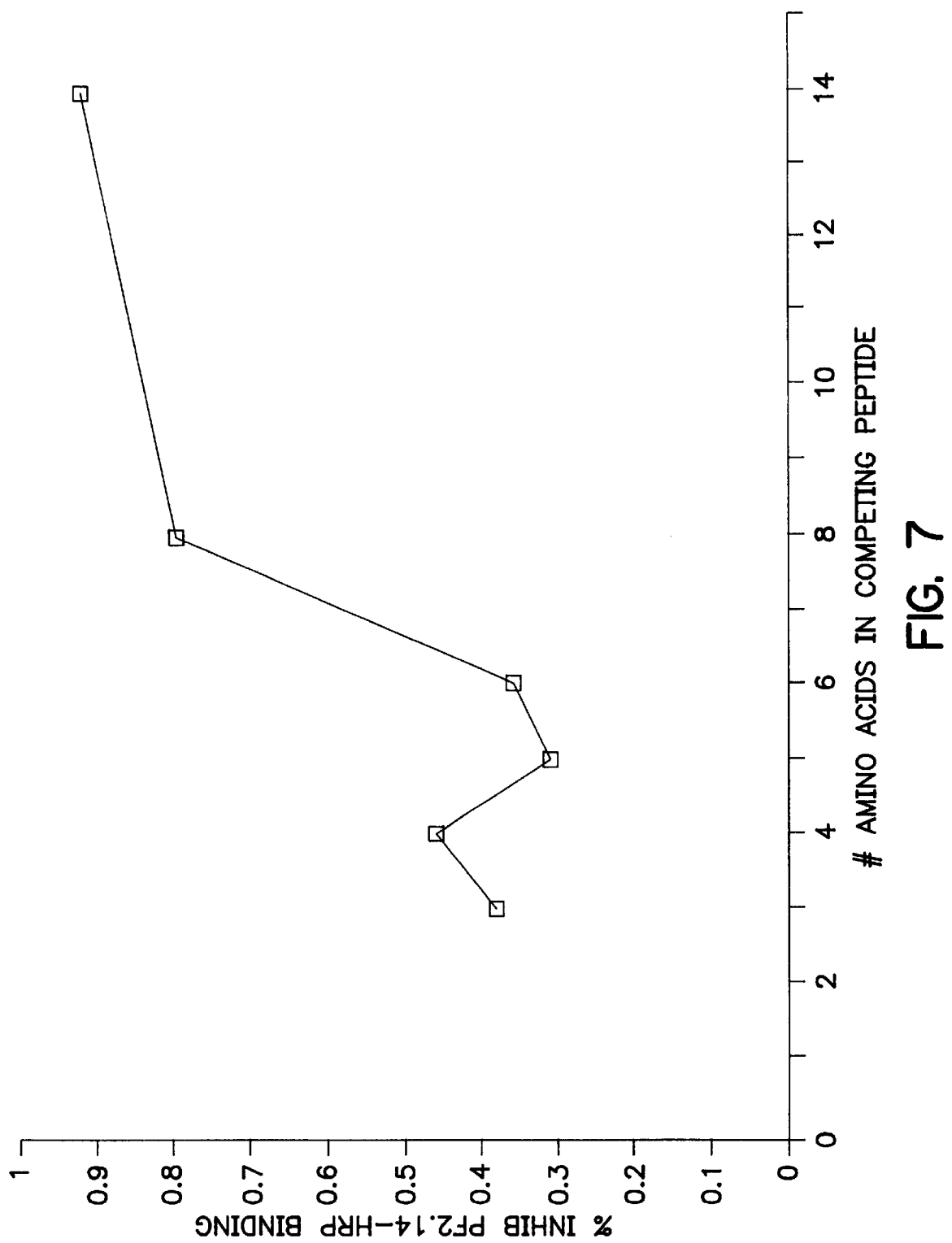
FIG. 7 is an illustration of the critical epitope size for recognition by monoclonal antibody 5-3B.

The relative abilities of peptides of various lengths to compete with HRP-PF2.14 indicated that the critical epitope size for recognition by 5–3B is between 6 and 8 amino acids (FIG. 7).

EXAMPLE XI
Preparation of Antibodies to the Prothrombin Calcium-dependent Conformer The antibodies were prepared and purified as described by Tai, N. M., 255 J. Biol. Chem. 2790 (1980), except that the immunogens were human prothrombin and human prothrombin fragment F1, and not bovine prothrombin. These antibodies recognize F1, prothrombin, and F1.2 in their native calcium-dependent conformation.

EXAMPLE XII
Preparation of HRP-labeled Antibodies to the Prothrombin Calcium-dependent Conformer Antibodies to the prothrombin calcium-dependent conformer were coupled to HRP using SPDP as the crosslinking agent and the procedure of Carlsson (see above). The difference between this example and that of Example I is that both antibody and HRP were first thiolated by reaction with SPDP. Approximately one pyridyldisulfidate site was introduced per mole of HRP. Thiolated HRP was reduced using dithiothreitol in coupling buffer at pH 4.5 and gel filtered on Sephadex G-25™, equilibrated in coupling buffer at pH 7.5, then reacted with the thiolated antibody at pH 7.5 for 45–60 minutes at room temperature. Incubation molar ratios were selected to yield conjugates with average loading between 2–5 mol HRP/mol antibody. SDS-PAGE in 7.5% homogenous gel confirmed the presence of conjugate with a molecular weight greater than 150,000 daltons. XIII. F1.2 Sandwich ELISA The F1.2 ELISA is a two-stage, sandwich immunoassay for human F1.2 which employs as capture the 5–3B monoclonal antibody which is specific for the F1.2 carboxyl terminal.

The microtitration plate used in the assay was prepared by incubating 0.4 μg 5–3B (in a 150 mM NaCl, 20 mM tris, pH 7.2 buffer solution) per well for 18 hours at room temperature. This amount of antibody saturated the well under these immobilization conditions. For each well, contents were aspirated, then 150 μL blocking solution (1% ovalbumin, 2.5% sucrose, 150 mM NaCl, 20 mM tris, 0.05% Tween-20™, pH 7.2) was added. After an hour incubation at room temperature, well contents were again aspirated. The plate was allowed to dry overnight at room temperature then stored in a mylar foil pouch containing a desiccant packet at 4° C.

Calibrators and controls used in the assay were prepared by addition of purified F1.2 to F1.2-depleted human plasma. Prior to depletion, citrated normal plasma was mixed at a 9:1 (v:v) ratio with a buffered, plasma-stabilizing solution. Stripping was accomplished by $BaSO_4$ adsorption of the plasma (0.22 g $BaSO_4$/mL plasma) twice. This procedure removed proteins containing gamma-carboxyglutamic acid residues including prothrombin and F1.2. Purified F1.2 was added to the adsorbed plasma to yield calibrators containing 0, 0.25, 1.0, 3.0, 6.0, and 10 nM F1.2, and controls containing 0.5 nM and 7.0 nM F1.2, respectively. The calibrators and controls were lyophilized in 1.0 mL aliquots and required reconstitution with a buffered solution prior to use. Preparation of the HRP-labeled anti-calcium dependent prothrombin conformer antibody used in the assay has been described above in Example XII. This antibody was lyophilized in a rabbit serum-based matrix and required reconstitution with a protein-based buffered solution prior to assay use as the detection antibody.

An appropriate sample for this assay was heparinized plasma containing at least a 30% normal level of antithrombin III. Prior to assay, plasma was mixed at a 9:1 (v:v) ratio with a buffered sample treatment reagent used to increase assay sensitivity. Plasma samples with greater than 10 nM of F1.2 can be measured by diluting as necessary with the 0 nM F1.2 calibrator to allow measurement within the assay's working range of 0–10 nM F1.2, as seen in Table 4.

TABLE 4

F1.2 ELISA: PARALLELISM BETWEEN SAMPLE AND CALIBRATOR

| DILUTION FACTOR | F1.2 (nM) | | | |
|---|---|---|---|---|
| | SITE A | | SITE B | |
| | DILUTED | NEAT* | DILUTED | NEAT* |
| Sample #1** | | | | |
| 1/2 | >10 | NA | 9.68 | 19.4 |
| 1/4 | 5.28 | 21.1 | 4.87 | 19.5 |
| 1/8 | 2.68 | 21.4 | 2.39 | 19.1 |
| 1/16 | 1.40 | 22.4 | 1.37 | 21.9 |
| 1/32 | 0.69 | 22.1 | 0.67 | 21.4 |
| | Mean (SD): 21.7 (0.6) | | 20.3 (1.3) | |
| Sample #2 | | | | |
| 1/2 | 8.19 | 16.4 | 7.69 | 15.4 |
| 1/4 | 3.94 | 15.8 | 3.78 | 15.1 |
| 1/8 | 2.00 | 16.0 | 1.98 | 15.8 |
| 1/16 | 1.01 | 16.2 | 1.12 | 17.9 |
| 1/32 | 0.52 | 16.6 | 0.62 | 19.8 |
| | Mean (SD): 16.2 (0.3) | | 16.8 (2.0) | |

*Calculated from F1.2 concentration in diluted sample divided by appropriate dilution factor.
**Samples 1 and 2 were prepared by F1.2 addition to heparinized plasma of 2 normal donors.

Figure 8:
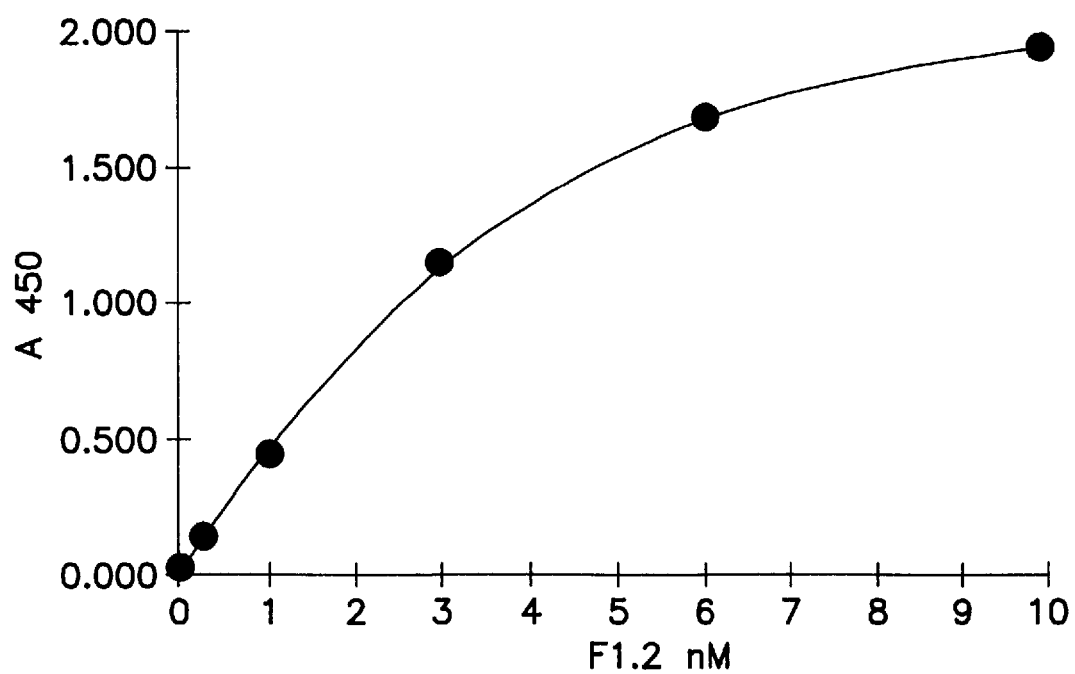
FIG. 8 is an ELISA calibration curve showing absorbance (measured at 450 nm) being proportional to the F1.2 concentration.

The plasma sample, calibrator (0–10 nM F1.2 ), or control (Levels I, II) was incubated for 60 minutes at room temperature with the coated microtitration well. Unbound proteins including prothrombin were removed by washing. Washing was performed by aspirating well contents, filling the well with 300 μL buffered wash solution, then aspirating contents; filling and aspiration was repeated four times. In the second stage, bound F1.2 was tagged by HRP-labeled antibodies to the prothrombin calcium-dependent conformer during a 60 minute incubation at room temperature. A second wash removed unbound HRP-labeled antibody. Bound HRP activity was determined using a tetramethylbenzidine (TMB)/hydrogen peroxide (1:1 mixture) indicator system (color development for 10 min) and 2N sulfuric acid as stopping reagent. Absorbance measured at 450 nm was proportional to the F1.2 concentration (FIG. 8). Volumes for sample, calibrator, control, detection antibody, TMB/hydrogen peroxide mixture, and sulfuric acid were each 100 uL/well.

XIV. Analytical Performance of the F1.2 ELISA

Assay sensitivity (i.e., the minimum F1.2 level distinguishable from the 0 nM F1.2 calibrator) is 0.05 nM F1.2. To determine this value, multiple replicates of the 0 nM F1.2 calibrator were assayed, and the F1.2 concentration associated with the mean absorbance at 450 nm plus two standard deviations was extrapolated from a calibration curve.

The assay is specific for at least 0.23 nM F1.2 in the presence of 1.5 $\mu$M prothrombin. Recovery of F1.2 from a buffer-based system containing 1.5 $\mu$M purified prothrombin and from heparinized plasma containing approximately 1.5 $\mu$M prothrombin averaged 92% and 98%, respectively, as seen in Table 5.

TABLE 5

F1.2 RECOVERY IN PRESENCE OF PROTHROMBIN

| MATRIX | F1.2 RANGE EVALUATED (nM) | % RECOVERY Mean | SD | N |
|---|---|---|---|---|
| Buffer + 1.5 $\mu$M prothrombin | 0.23–23 | 92 | 13 | 3 |
| Normal Plasma | 0.5–10 | 98 | 13 | 23 |

Crossreactivity with prothrombin or other plasma-based proteins would have resulted in recoveries greater than 100%. In addition, no major interference was detected in the assay by triglyceride, hemoglobin, or bilirubin (Table 6).

TABLE 6

F1.2 ELISA SPECIFICITY

| Analyte | Concentration | F1.2 Recovery % |
|---|---|---|
| Prothrombin | 1.5 $\mu$M | 98 |
| Triglyceride | 500 mg/dL | 103 |
| Hemoglobin | 100 mg/dL | 111 |
| Bilirubin | 20 mg/dL | 97 |

Measured imprecision is comparable to other sandwich ELISA's (Hoek, J. A., 34 Clin. Chem. 2058–2062 (1988)). Coefficients of variation determined at two sites were less than 9% by intra-assay imprecision and less than 11% by inter-assay imprecision at both Control Levels I and II as seen in Table 7.

TABLE 7

F1.2 ELISA REPRODUCIBILITY

| | F1.2 (nM) | | | |
|---|---|---|---|---|
| | Mean | SD | N | CV % |
| INTRA-ASSAY | | | | |
| Level I | | | | |
| Site A | 0.487 | .012 | 20 | 2.5 |
| Site B | 0.587 | .054 | 20 | 9.2 |
| Level II | | | | |
| Site A | 6.49 | 0.44 | 20 | 6.8 |

TABLE 7-continued

F1.2 ELISA REPRODUCIBILITY

| | F1.2 (nM) | | | |
|---|---|---|---|---|
| | Mean | SD | N | CV % |
| Site B | 6.56 | 0.42 | 20 | 6.4 |
| INTER-ASSAY | | | | |
| Level I | | | | |
| Site A | 0.498 | .043 | 20 | 8.6 |
| Site B | 0.485 | .053 | 13 | 10.6 |
| Level II | | | | |
| Site A | 6.97 | 0.53 | 20 | 7.6 |
| Site B | 6.92 | 0.56 | 12 | 8.1 | xv. Clinical Performance of the F1.2 ELISA

F1.2 levels were measured using the ELISA assay of Example XIII above, in a healthy population, patients with thrombosis or conditions associated with thrombotic risk, and patients on anticoagulant therapy. Mean F1.2 concentration for a healthy population under 45 years of age was 1.5±0.6 nM (±SD; n=30), agreeing with values measured by radioimmunoassay (Bauer, K., 70 Blood 343–350 (1987)). Incidence of elevated F1.2 (>2.7 nM) as shown in Table 8 was 38% (15/39 patients) in conditions predisposing to thrombosis compared to 100% (16/16 patients) in established thrombotic conditions. F1.2 levels were greater than 20 nM in two cases of sickle cell anemia and one case of venous thrombosis.

TABLE 8

F1.2 IN PATIENTS WITH THROMBOSIS AND CONDITIONS ASSOCIATED WITH THROMBOTIC RISK

| CLINICAL CONDITION | INCIDENCE OF ELEVATED F1.2* (No. with F1.2 >2.7 nM/No. Pts.) |
|---|---|
| THROMBOSIS | |
| Stroke | 1/1 |
| DIC | 2/2 |
| Myocardial Infarction | 8/8 |
| Venous Thrombosis | 5/5 |
| Total | 16/16 (100%) |
| THROMBOTIC RISK | |
| Cancers | 3/6 |
| SLE or LUPUS anticoagulant | 2/5 |
| Unstable Angina | 3/6 |
| Sickle Cell Disease | 5/13 |
| PNH | 0/1 |
| Peripheral Vascular Disease | 1/2 |
| Diabetes Mellitus | 1/6 |
| Total | 15/39 (38%) |

*Reference Range (95% CI) for F1.2: 0.3–2.7 nM (30 healthy donors, aged 18–45 yrs; Normal distribution; Mean ± 2SD = 1.5 ± 1.2 nM)
F1.2 levels were suppressed (less than 0.3 nM) in five patients on long-term coumadin therapy (Table 9).

TABLE 9

F1.2 IN PATIENTS ON ORAL ANTICOAGULANT THERAPY

| CLINICAL CONDITION (All on coumadin) | F1.2 (nM) | COMMENT |
|---|---|---|
| Liver Cancer | 0.21 | Long-term Rx |
| SLE | 0.21 | Long-term Rx |

TABLE 9-continued

F1.2 IN PATIENTS ON ORAL ANTICOAGULANT THERAPY

| CLINICAL CONDITION (All on coumadin) | F1.2 (nM) | COMMENT |
|---|---|---|
| SLE | 0.25 | Long-term Rx |
| Mitral Valve Replacement | 0.13 | Long-term Rx |
| Congestive Heart Failure | 1.03 | Only 5 days Rx |
| Lupus Anticoagulant | 0.19 | Also Org 10172 |

One patient with normal F1.2 level had been on this therapy for only 5 days. In patients receiving continuous heparin infusion (Table 10) for treatment of sudden cardiac death/myocardial infarction (4 patients) or unstable angina (3 patients), F1.2 levels decreased for all patients with exception of the patient who suffered sudden cardiac death and whose clinical course was complicated by florid disseminated intravascular coagulation.

TABLE 10

F1.2 IN PATIENTS ON HEPARIN THERAPY

| PATIENT'S CLINICAL CONDITION | NO. DAYS POST-ADMIT | F1.2 (nM) On Consecutive Days | | |
|---|---|---|---|---|
| (Cont. Hep. Infusion) | For Day A | Day A | Day B | Day C |
| Sudden Cardiac Death* | 2 | 4.7 | 4.4 | 4.5 |
| Myocardial Infarction | 1 | 14.2 | 4.4 | nd |
| Myocardial Infarction | 3 | 5.8 | 2.0 | nd |
| Myocardial Infarction | 6** | 9.2 | 2.2 | 0.8 |
| MI/Unstable Angina | Unk. | 3.3 | 1.8 | nd |
| Unstable Angina | 4 | 7.1 | 4.4 | nd |
| Unstable Angina | 4 | >10 | 5.4 | 1.4 |

*Clinical course marked by florid disseminated intravascular coagulation
**Recurrent chest pain two days prior to first F1.2 sample.
nd = Not done These data indicate F1.2 levels as measured by the described F1.2 ELISA may be useful for assessing individual thrombotic risk and monitoring efficacy of anticoagulant therapy.

We claim:

1. A monoclonal antibody and fragments thereof that specifically bind to an epitope on the carboxy terminus of a prothrombin activation peptide, wherein said epitope comprises the amino acid sequence -Ser-Asp-Arg-Ala-Ile-Glu-Gly-Arg-OH, and wherein said monoclonal antibody is secreted by the hybridoma identified as ATCC No. HB 10291.

2. A method of immunologically assaying for prothrombin activation peptide F1.2 in a sample, comprising:

a) coating a solid phase with a monoclonal antibody according to claim 1;

b) adding sample to said solid phase;

c) adding a labeled antibody having specificity for said monoclonal antibody or prothrombin activation peptide F1.2 and incubating; and d) detecting the immunoreaction by measuring said label, thereby determining the amount of F1.2.

3. A method according to claim 2, wherein said sample is selected from the group consisting of serum, plasma, whole blood, urine, cerebral spinal fluid or synovial fluid.

4. A method according to claim 2, wherein said label is a material selected from the group consisting of horseradish peroxidase, glucose-6-phosphate dehydrogenase, alkaline phosphatase, beta-galactosidase, fluoroisothioyanate, rhodamine, fluorescein, luciferase, radioisotopes and particles.

5. A method of immunologically assaying for prothrombin activation peptide F1.2 in a sample, comprising an immunoassay wherein a monoclonal antibody according to claim 1 is used as the capture antibody and wherein the immunoassay is a method selected from the group consisting of competitive inhibition immunoassays, single step immunoassays and agglutination immunoassays.

6. A diagnostic kit for immunologically assaying for prothrombin activation peptide F1.2 in a sample comprising a monoclonal antibody according to claim 1 coated on a solid phase.

7. A diagnostic kit for immunologically assaying for prothrombin activation peptide F1.2 in a sample comprising a monoclonal antibody derived from the hybridoma identified as ATCC No. HB 10291.

8. A hybridoma that secreted by an antibody consisting of the hybridoma identified as ATCC No. HB 10291.

* * * * *